United States Patent [19]

Lekholm

[11] Patent Number: 5,097,831
[45] Date of Patent: Mar. 24, 1992

[54] RATE-RESPONSIVE PACEMAKER WITH CIRCUITRY FOR PROCESSING MULTIPLE SENSOR INPUTS

[75] Inventor: Anders Lekholm, Northridge, Calif.

[73] Assignee: Siemens-Pacesetter, Inc., Sylmar, Calif.

[21] Appl. No.: 510,337

[22] Filed: Apr. 16, 1990

[51] Int. Cl.[5] .................................... A61N 1/368
[52] U.S. Cl. .................................... 128/419 PG
[58] Field of Search .................................... 128/419 PG

[56] References Cited

U.S. PATENT DOCUMENTS

| | | | |
|---|---|---|---|
| 4,867,161 | 9/1989 | Schaldach | 128/419 PG |
| 4,873,980 | 10/1989 | Schaldach | 128/419 PG |
| 4,895,151 | 1/1990 | Grevis et al. | 128/419 PG |

Primary Examiner—William E. Kamm
Assistant Examiner—Kennedy J. Schaetzle
Attorney, Agent, or Firm—Leslie S. Miller

[57] ABSTRACT

An implantable rate-responsive pacemaker is disclosed wherein two or more sensors indicative of physiological demand are utilized in a fashion designed to realize the advantages of both sensors in a circuit producing a rate command signal which is used to operate the pacemaker at an optimum pacing rate which will closely match physiological need of the patient. A switch matrix monitors processed signals from the sensors to select a unique set of numerical coefficients indicated by the processed sensor signals. The selected set of numerical coefficients are used as weighting factors to weight the impact of each of the sensor signals in the calculation of a selected rate.

31 Claims, 4 Drawing Sheets

RATE-RESPONSIVE PACEMAKER WITH CIRCUITRY FOR PROCESSING MULTIPLE SENSOR INPUTS

BACKGROUND OF THE INVENTION

FIELD OF THE INVENTION

The present invention relates generally to rate-responsive cardiac pacemakers, and more particularly to an implantable rate-responsive pacemaker wherein two or more sensors indicative of physiological demand are utilized in a fashion designed to realize the advantages of both sensors in a circuit producing a rate command signal which is used to operate the pacemaker at an optimum pacing rate which will closely match physiological need of the patient.

A pacemaker is an implantable medical device which delivers electrical stimulation pulses to a patient's heart in order to keep the heart beating at a desired rate. Early pacemakers provided stimulation pulses at a fixed rate or frequency, such as 70 pulses per minute (ppm), thereby maintaining the heartbeat at that fixed rate. Subsequently, pacemakers were designed to not only stimulate the heart, but also to monitor the heart. If a natural heartbeat was detected within a prescribed time period (usually referred to as the "escape interval"), no stimulation pulse was delivered, thereby allowing the heart to beat on its own without consuming the limited power of the pacemaker or interfering with the normal operation of the heart. Such pacemakers are referred to as "demand pacemakers" because stimulation pulses are provided only as demanded by the heart.

Early demand pacemakers had a fixed base rate associated with them. In later versions, the base rate was programmably selectable, and thereafter became commonly known as the "programmed rate." If the heart was able to beat on its own at a rate exceeding the base (or programmed) rate, then no stimulation pulses were provided. However, if the heart was not able to beat on its own at a rate exceeding the base rate, then stimulation pulses were provided to ensure that the heart would always beat at least at the base (or programmed) rate. Such operation was achieved by simply monitoring the heart for a natural beat during the escape interval. If natural activity was sensed, the timer which defined the escape interval was reset. If no natural activity was sensed, a stimulation pulse was provided as soon as the escape interval had timed out. Changing the base (or programmed) rate was accomplished by simply changing the duration of the escape interval.

In recent years, rate-responsive pacemakers have been developed which automatically change the rate at which the pacemaker provides stimulation pulses as a function of a sensed physiological parameter. The physiological parameter provides some indication of whether the heart should beat faster or slower, depending upon the physiological needs of the pacemaker user. Thus, for example, if a patient is at rest, there is generally no need for a faster-than-normal heart rate, so the rate-responsive pacemaker maintains the "base rate" at a normal value, such as 60 pulses per minute (ppm).

However, if the patient is exercising, or otherwise physiologically active, there is a need for the heart to beat much faster, such as, for example, 100 beats per minute. For some patients, the heart is not able to beat faster on its own, so the pacemaker must assist. In order to do this effectively, the physiological need for the heart to beat faster must first be sensed, and the "base rate" of the rate-responsive pacer must be adjusted accordingly. Hence, rate-responsive pacemakers are known in the art which increase and decrease the "base rate" as a function of sensed physiological need.

Numerous types of sensors are taught in the art for use with a rate-responsive pacer. In each, an increase or decrease in the parameter being monitored signals a need to increase or decrease the rate at which pacing pulses are provided. Note, as used herein, the term "pacing rate" refers to the rate at which the pacer provides stimulation pulses, or in the case of demand pacers, the rate at which the pacer would provide stimulation pulses in the absence of naturally occurring heartbeats.

One common type of sensor is an activity sensor which senses the physical activity level of the patient. See, for example, U.S. Pat. No. 4,140,132, to Dahl, and U.S. Pat. No. 4,485,813, to Anderson et al. In accordance with the teachings of Dahl or Anderson et al., a piezoelectric crystal is used as an activity sensor. Such a crystal generates an electrical signal when subjected to physical movement and stress according to well known principles. The electrical signal generated by the crystal may be processed and used to vary the pacing rate.

Other types of sensors used in prior art rate-responsive pacers include sensors that sense respiration rate, respiratory minute volume, blood oxygen level, blood and/or body temperature, blood pressure, the length of the Q-T interval, the length of the P-R interval, etc. All of the sensors which may be used in rate-responsive pacers have particular advantages and disadvantages.

The next generation of rate-responsive pacemakers will use two or more sensors simultaneously to control the pacing rate. It will be appreciated by those skilled in the art that the combination of signals from two or more sensors to be used to control pacing rate is a difficult and complex task.

The goal of a system using two or more sensors should be to utilize the best properties of each of the sensors, while eliminating or minimizing their drawbacks. For example, an activity sensor will react very quickly to the onset of exercise, closely mimicking the response of the sinus node in a healthy heart. However, an activity sensor does not measure any true physiological variable of the body, and as such may be a poor predictor of work level and of the optimum heart rate. Alternately, a sensor measuring respiratory minute volume or venous blood temperature will provide a very good correlation to the level of exercise at higher levels of exercise. However, the sensor response of a respiratory minute volume sensor or venous blood temperature sensor is much slower than the response of the SA node, typically of the order of sixty to ninety seconds. Thus, it may be seen that all single sensor systems will have both significant advantages and disadvantages.

Theoretically, a combination of an activity sensor and a respiratory minute volume sensor or venous blood temperature sensor could be used to control pacing rate in a manner which is more physiologic than either of the sensors separately. The combination technique may, however, prove quite complex in its implementation. For example, a summation and averaging of the two signals would not be optimum for the following reasons. At the onset of exercise, the activity sensor would deliver a signal, while the other sensor would not yet have reacted. Thus, the onset of heart activity would be slower than in the case of using activity alone.

During prolonged exercise, the good sensor response of the respiratory minute volume or blood temperature sensor would be averaged with the poorer response of the activity sensor. In this case, the result would not be as accurate as using the respiratory minute volume or blood temperature sensor alone. During prolonged exercise at a low level, the activity sensor may be as good as the respiratory minute volume or blood temperature sensor because the latter two are inaccurate at low levels of exercise. In the case of a false positive indication of activity of the activity sensor (caused, for example, by riding in a car on a bumpy road), the poor response of the activity sensor would be averaged with the good response of the respiratory minute volume or blood temperature sensor. Thus, the result again would not be as accurate as using the respiratory minute volume or blood temperature sensor alone.

Another possible technique which may be used to combine the inputs from two sensors would be to take the highest value of the two sensors. This would in at least some cases yield a better result than the averaging technique discussed above. This combination would not, however, eliminate the erroneous increase in pacing rate resulting from external vibration picked up by the activity sensor.

Thus, while this technique could give a better response to exercise in some situations, it would not eliminate problems occurring due to erroneous responses of the sensors. In addition to the problem of external vibration mentioned above, if the other sensor used was a blood temperature sensor, the shortcomings of this sensor would be propagated. For example, heavy clothing or external temperature change would result in erroneous changes to the pacing rate. In short, it will be perceived by those skilled in the art that it is difficult and complex to utilize inputs from more than one sensor in an intelligent fashion which will enhance the advantages of each sensor without proliferating the drawbacks of the sensors.

In concurrently filed U.S. Patent Application Ser. No. 07/509,645, also entitled "Rate-Responsive Pacemaker With Circuitry for Processing Multiple Sensor Inputs," a system is disclosed which uses the concept of a rate matrix for combining inputs from two or more sensors. That application is hereby incorporated herein by reference. In the simplest embodiment taught in that application, the concept of a two-dimensional rate matrix is used. The coordinates of the rate matrix are the processed signals from sensors, with the value of one of the processed signals being used to select one axis (the columns, for example) of the rate matrix, and the value of the other of the processed signals being used to select the other axis (the rows, for example) of the rate matrix.

The processed sensor signals are digitized into a desired number of increments corresponding to the size of the rate matrix, which may be, for example, a 10 by 10 matrix. The rate matrix has in its cells values which are selected rate signals. Thus, the rate matrix is essentially a look-up table, with the value of the selected rate signal being unique and depending on the value of the processed signals from the sensors. This selected rate may then supplied to a reaction and recovery time limiting circuit, with the output from the reaction and recovery time limiting circuit being supplied as the sensor-indicated rate signal to the other circuitry of the pacemaker to control the pacing rate of the device.

The values inscribed in the rate matrix may be programmable to tailor the rate matrix for different lifestyles. Alternately, multiple rate matrices may be provided with the specific rate matrix to be used being programmable.

In the preferred version of the invention disclosed in the above-identified application, the versatility and intelligence of the system is enhanced through the use of a switch matrix which is used to select which of a plurality of rate matrices will be used. There are as many rate matrices as there are cells in the switch matrix. Processing circuitry consisting of logic circuits and timing circuits are used to monitor the processed signals from the sensors and supply inputs enabling the selection of a row and a column in the switch matrix.

The outputs of the processing circuitry are used to select a cell in the switch matrix which corresponds to the exact set of conditions currently being encountered by the sensors. Thus, for example, if the switch matrix is five by seven, there are 35 different sets of conditions which the two sensors may be encountering, and there are 35 corresponding rate matrices which may be used by the system.

The particular rate matrix which is selected by the switch matrix has as inputs the processed signals from the sensors. The selected rate matrix will output a particular selected rate which is used to control the paced rate of the pacemaker. It is apparent that in the example given above, there are 35 different rate matrices, each of which would have 100 different values contained therein. These values would all be contained in memory in the form of look-up tables.

It will be appreciated by those skilled in the art that this system is excellent in serving its function of combining signals from two or more sensors in a manner which retains the advantages of both systems while largely eliminating the disadvantages of each system. In fact, the system of the above-identified application has only one significant disadvantage. In its preferred embodiment, it requires a large amount of memory which may be difficult to implement within the space constraints of a pacemaker.

The example described above would require the equivalent of 3500 two or three digit numbers denoting pacemaker rates to be stored in memory, thus requiring approximately 28K of memory for the rate matrices alone. Since pacemakers at the present time have a total of approximately 8K of memory, it will be appreciated that until larger memories are reduced in size this memory requirement may be difficult to implement within the space limitations of a pacemaker.

It is accordingly the objective of the present invention that it provide a system with the advantages of the system described in the above-identified patent application, but without the large memory requirement. Such a system will utilize inputs from two or more sensors to provide a sensor-indicated rate signal, which will control the pacing rate of the pacemaker. It is an objective of the system of the present invention to utilize the best properties of each of the sensors, while minimizing or eliminating their drawbacks. The control strategy must be of a complexity sufficient to provide as an output a highly flexible sensor-indicated rate signal which will accurately follow a control strategy paralleling the physiological response of a healthy heart.

It is a further objective of the present invention that its implementation be relatively simple and easy to accomplish in a pacemaker, which is necessarily limited in size since it is an implanted device. The system of the present invention should be useable with at least two sensors, but should also be capable of working with more than two sensors. The system should also be economic of power, not requiring more power to operate than do other rate-response systems. Finally, it is also an objective that all of the aforesaid advantages and objectives be achieved without incurring any substantial relative disadvantage.

SUMMARY OF THE INVENTION

The disadvantages and limitations of the background art discussed above are overcome by the present invention. With this invention, two or more sensors are used to supply inputs to circuitry which will extract relevant information from each sensor and combine these signals in an optimum way so as to produce a signal which controls the rate of the pulse generator output. This circuitry is hereafter called a rate-response processor. In the preferred embodiment, two sensors are used, with one of them being an activity sensor (which responds quickly) and the other being a more physiologically responsive (but slower responding) sensor such as a blood temperature sensor or a respiratory minute volume sensor. Other sensors which could be used include a blood oxygen sensor (either blood oxygen saturation or blood oxygen partial pressure), a pH sensor, a $pCO_2$ sensor, a QT interval sensor, a respiratory rate sensor, a stroke volume sensor, an intracardiac electrocardiogram QRS morphology change sensor, etc. Alternately, the system may be used to combine signals from two sensors, one of which has a good specific response for low levels of exercise and the other of which has a good specific response for high levels of exercise. In either case, processing circuitry is used to condition the raw signals from the sensors into processed sensor signals.

A switch matrix and associated processing circuitry for driving the switch matrix similar to that used in the above-identified patent application is utilized by the present invention. However, in the embodiment of the present invention, the rate matrices containing numerical values representing specific pacing rates are replaced by matrices containing numerical coefficients for a formula which defines the relationship between the processed sensor signals and the pacing rate. These matrices are called coefficient matrices. Thus, the switch matrix is used to select which of a plurality of sets of numerical coefficients for a weighting formula will be used. There are as many sets of numerical coefficients as there are cells in the switch matrix.

For the two sensor system used as an example in the preferred embodiment, the formula or transfer function would be Rate $= X \cdot S_1 + Y \cdot S_2 + Z$, where X, Y, and Z are numerical coefficients, $S_1$ is the processed signal from Sensor 1, $S_2$ is the processed signal from Sensor 2, and Rate denotes the resulting pacemaker stimulating rate. Thus, X is the weighting factor given to the output from the first sensor, Y is the weighting factor given to the output from the second sensor, and Z is an offset factor. For each cell in the switch matrix, there would be one set of three numerical coefficients stored in memory. This is an example only. The formula may be made more complex to accommodate nonlinear transfer functions.

In its simplest form the coefficient matrix is a $1 \times 1$ matrix; in other words, the switch matrix reflects coefficients for one formula covering all input values from both sensors. The outputs of the processing circuitry are used to select a cell in the switch matrix which corresponds to the exact set of conditions currently being encountered by the sensors. Thus, for example, if the switch matrix is five by seven, there may be seven different conditions which the processed signal from the first sensor may be evidencing. Similarly, there may be five different conditions which the processed signal from the second sensor may be evidencing. Thus, there are 35 different sets of conditions which the two sensors may be encountering, and there are 35 corresponding sets of numerical coefficients which may be used by the system.

Thus, for a two sensor system, the memory would be required to store 105 numerical coefficients therein. This may be contrasted to the system of the above-identified patent application, in which 3500 rates must be stored. It will thus be appreciated that the present invention requires significantly less memory than the system of the above-identified application.

The particular set of numerical coefficients which are selected by the switch matrix will be supplied to calculating circuitry, which also has as inputs the processed signals from the sensors. The calculating circuitry will implement the formula described above to calculate a selected rate which is used to control the paced rate of the pacemaker. Thus, once the switch matrix indicates which set of numerical coefficients are to be used, the selected rate may be computed.

This selected rate is then supplied to a reaction and recovery time circuit, as is conventional in the art. The reaction and recovery time circuit is a device which will limit how quickly the pacing rate can increase or decrease. The output from the reaction and recovery time circuit is supplied as the sensor-indicated rate signal to the other circuitry of the pacemaker, and will control the pacing rate of the device. An alternate approach to performing the reaction and recovery time functions would be to include these functions in the conditions governing the switch matrix, or on the input side of the system rather than on the output side. Since the reaction and recovery time circuit tends to mask the sensor output, it is normally advantageous to place the reaction and recovery time circuit after the selected rate is computed.

In the preferred embodiment, the values inscribed as the various numerical coefficients are programmable. An external programmer is used to program the values of the numerical coefficients. The numerical coefficients may thus be tailored for individual conditions and lifestyles for each patient, with factors such as age, activity level, and physical condition being used to select the values stored as the various numerical coefficients. The external programmer may embody an expert system to guide the physician to the proper numerical coefficient values. The switch matrix is also preferably programmable.

Alternately, multiple banks of numerical coefficients (coefficient matrices) may be provided in the implanted device with the specific bank of numerical coefficients to be used being selectable by programming. The external programmer would be used to program which of the banks of numerical coefficients is to be selected. The different banks of numerical coefficients may be tailored for different lifestyles, ages, activity levels, or physical conditions.

It will thus be appreciated by those skilled in the art that the switch matrix is used to analyze the particular circumstances indicated by the signals from the sensors. A specifically designed set of numerical coefficients for use under the particular circumstances is indicated, and the selected rate is calculated using the chosen set of numerical coefficients, and used to control the pacing rate of the pacemaker. It will be recognized that in systems using more than two sensors, a multi-dimension matrix may be used to select the appropriate numerical coefficients. For example, in a three sensor system, a three dimensional switch matrix would be used.

In an alternate embodiment, the processed signals from one of the sensors are supplied to a switch matrix via processing circuitry. Based on the particular circumstances indicated by the signal from the one sensor, a particular set of numerical coefficients is indicated. The selected numerical coefficients and the processed signals from both sensors are supplied to the calculating circuitry, where a selected rate is calculated. That selected rate is then used to control the pacing rate of the pacemaker.

It may therefore be seen that the present invention teaches a system which will utilize inputs from two or more sensors to provide a sensor-indicated rate signal, which will control the pacing rate of the pacemaker. The system of the present invention can utilize the best properties of each of the sensors, while minimizing or eliminating their drawbacks. The control strategy is of a complexity sufficient to provide as an output a highly flexible sensor-indicated rate signal which will accurately follow a control strategy paralleling the physiological response of a healthy heart. In addition to being highly flexible, the control strategy of the preferred embodiment of the present invention is also fully programmable by using the external programmer.

The implementation of the present invention is relatively simple and easy to accomplish in a pacemaker, and will not significantly increase either the size or the memory requirements of the pacemaker. The system of the present invention is useable with two sensors, and is capable of working with more than two sensors. The system is also economic of power, and does not require more power to operate than do other rate-response processors. Finally, all of the aforesaid advantages and objectives are achieved without incurring any substantial relative disadvantage.

DESCRIPTION OF THE DRAWINGS

These and other advantages of the present invention are best understood with reference to the drawings, in which.

DETAILED DESCRIPTION OF THE PREFERRED EMBODIMENT

Figure 1:
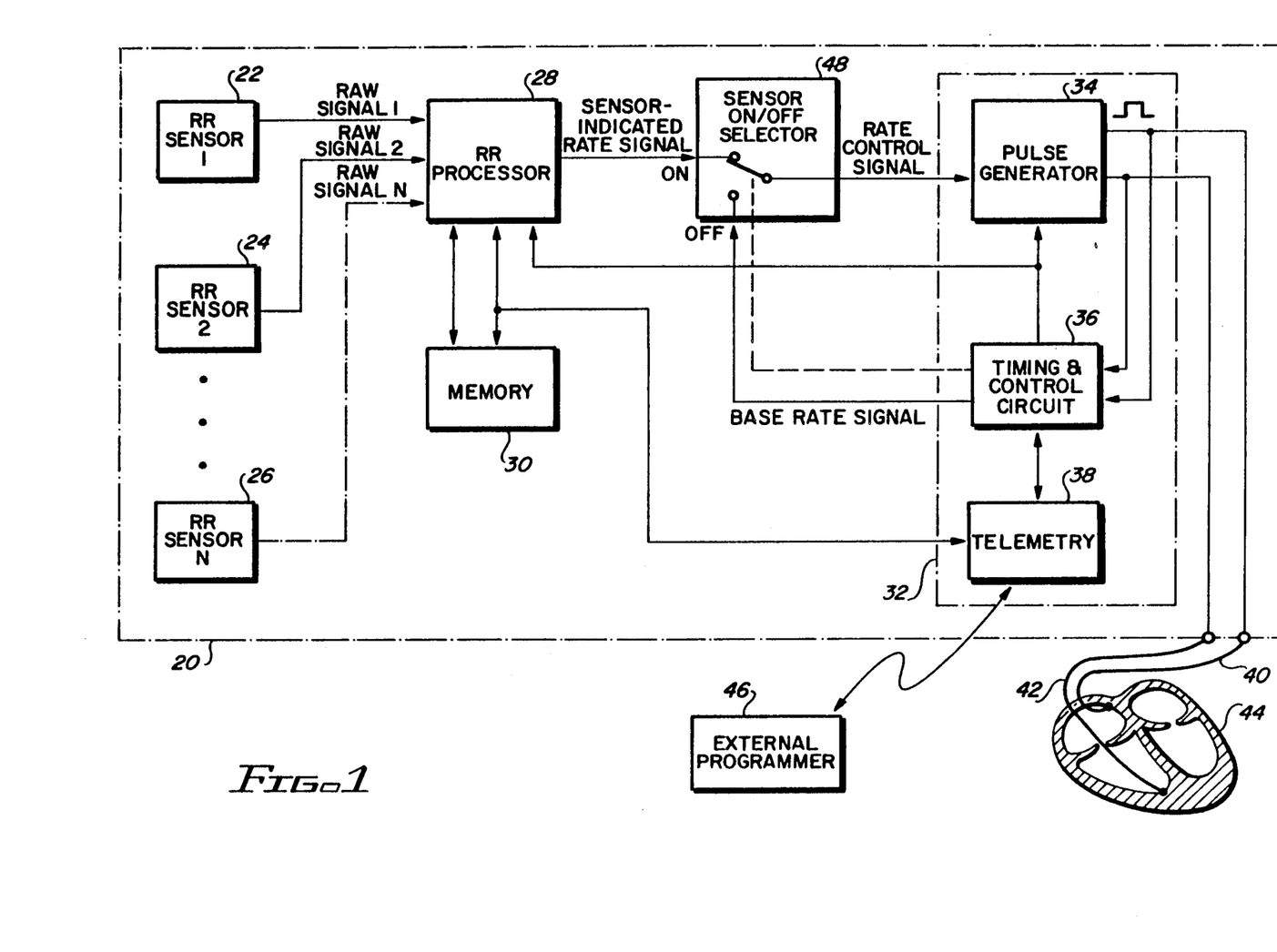
FIG. 1 is a functional block diagram of a rate-responsive pacemaker incorporating the features of the present invention.

The preferred embodiment is illustrated embodied in a rate-responsive pacemaker 20 shown in FIG. 1. The pacemaker 20 utilizes a first rate-responsive sensor 22 and a second rate-responsive sensor 24. The example illustrated as the preferred embodiment of the present invention utilizes two sensors, although more than two sensors could be utilized, as illustrated by an Nth rate-responsive sensor 26 illustrated in phantom lines in FIG. 1. The output of the first rate-responsive sensor 22 is identified as raw signal 1, and the output of the second rate-responsive sensor 24 is identified as raw signal 2.

The outputs of the first rate-responsive sensor 22 and the second rate-responsive sensor 24, the raw signal and the raw signal 2, respectively, are supplied to a rate-responsive processor 28. The rate-responsive processor 28 is the heart of the present invention, and its operation will be described in detail below. The rate-responsive processor 28 accesses a memory circuit 30, and produces as an output a sensor-indicated rate signal. The sensor-indicated rate signal is a signal which indicates the rate which the rate-responsive processor 28 has calculated the pacemaker 20 should use as the pacing rate, based on the inputs from the first rate-responsive sensor 22 and the second rate-responsive sensor 24.

The pacemaker 20 also includes a conventional pacemaker circuit 32 which typically includes at least a pulse generator 34, a timing and control circuit 36, and a telemetry circuit 38. The pulse generator 34 provides electrical pulses to two leads 40 and 42, which provide electrical contact with a patient's heart 44. The leads 40 and 42 may be either unipolar leads, bipolar leads, or other multi-pole leads, all of which are known in the art. It should be noted that while the system shown in FIG. 1 is a dual chamber pacemaker, the principles of the present invention could just as easily be applicable to a single chamber pacemaker.

An external programmer 46 is also used to send programming signals to the telemetry circuit 38. These programming signals are depicted symbolically as a wavy line in FIG. 1. It should be noted that signals may be sent either from the external programmer 46 to the pacemaker 20, or from the pacemaker 20 to the external programmer 46.

Functionally, the pulse generator 34 generates stimulation pulses supplied to the leads 40 and 42 at a rate determined by a rate control signal, which is an input to the pulse generator 34. These stimulation pulses, in turn, are delivered to the heart 44 through the leads 40 and 42 in a conventional manner. It should also be understood that although the first rate-responsive sensor 22 and the second rate-responsive sensor 24 are shown in FIG. 1 as being included within the pacemaker 20, one or both of the first rate-responsive sensor 22 and the second rate-responsive sensor 24 could also be included within, or coupled to, one of the leads 40 and 42. In addition, the first rate-responsive sensor 22 and/or the second rate-responsive sensor 24 cloud also be placed externally of the pacemaker 20.

The leads 40 and 42 also present electrical signals occurring within the heart 44, such as intracardiac P-waves and R-waves (evidencing natural cardiac activity of the atria and ventricles, respectively), to the timing and control circuit 36. Hence, for example, when programmed in a demand mode of operation, the pacemaker 20 is able to inhibit the generation of a pacing pulse when natural cardiac activity is sensed within a designated time period, in a conventional manner.

A more complete description of the pacemaker circuit 32 and its operation may be found in several patents. For example, note U.S. Pat. No. 4,232,679, entitled "Programmable Human Tissue Stimulator"; U.S. Pat. No. 4,686,988, entitled "Pacemaker System and Method for Measuring and Monitoring Cardiac Activity and for Determining and Maintaining Capture"; and U.S. Pat. No. 4,712,555, entitled "Physiologically Responsive Pacemaker and Method of Adjusting the Pacing Interval Thereof." While not disclosing the exact same pacemaker circuit 32 or circuits which are used in the preferred embodiment of the present invention, these patents nonetheless disclose the primary components of a conventional pacing system and teach the basic operation thereof. U.S. Pat. No. 4,232,679; U.S. Pat. No. 4,686,988; and U.S. Pat. No. 4,712,555 are hereby incorporated herein by reference.

In operation, the rate-responsive pacemaker 20 may operate in either a SENSOR ON mode or a SENSOR OFF mode. The selection of a desired mode of operation is controlled by a sensor on/off selector 48, shown functionally in FIG. 1 as a switch. The sensor on/off selector 48 connects either a base rate signal supplied from the timing and control circuit 36 or the sensor-indicated rate signal supplied from the rate-responsive processor 28 as the rate control signal input to the pulse generator 34. Control of the sensor on/off selector 48 is obtained from the timing and control circuit 36, which control may be selected by an appropriate programming signal received from the external programmer 46.

When the SENSOR OFF mode is selected, the sensor on/off selector 48 directs the base rate signal, generated by the timing and control circuit 36, to be the rate control signal input to the pulse generator 34. This base rate signal thus controls the pacing rate of the pacemaker 20 in a conventional manner.

When the SENSOR ON mode is selected, the rate control signal input to the pulse generator 34 is connected by way of the sensor on/off selector 48 to the sensor-indicated rate signal output from the rate-responsive processor 28. (It will of course be appreciated by those skilled in the art that there are other ways to accomplish the sensor on/off function.) The sensor-indicated rate signal, as mentioned above, is derived from the raw signal 1 and the raw signal 2 from the first rate-responsive sensor 22 and the second rate-responsive sensor 24, respectively.

Typically, the rate control signal may be thought of as simply a signal responsible for generating a trigger pulse at the timing out of an escape interval (also generated by the timing and control circuit 36). However, if natural cardiac activity is sensed during the escape interval, no trigger pulse is generated by the pulse generator 34 and the portion of the timing and control circuit 36 responsible for generating the escape interval is reset, thereby starting a new escape interval. Hence, regardless of the source of the rate control signal (either the base rate signal from the timing and control circuit 36 or the sensor-indicated rate signal from the rate-responsive processor 28), such signal may be overridden (if the pacemaker 20 is so programmed) by the sensing of natural cardiac activity.

Figure 2:
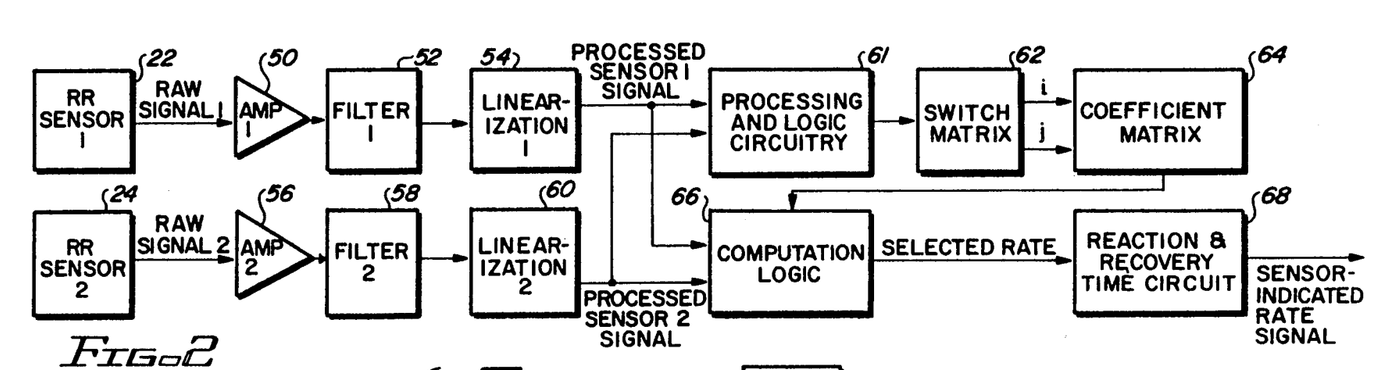
FIG. 2 is a functional block diagram of the rate-responsive processor of the pacemaker shown in FIG. 1.

Referring next to FIG. 2, one possible construction of the rate-responsive processor 28 of FIG. 1 is illustrated. In the preferred embodiment, signal processing circuitry is used to process raw signal 1 from the first rate-responsive sensor 22 and raw signal 2 from the second rate-responsive sensor 24. Such processing circuitry is known in the art and is not necessarily an integral part of the present invention. The amplification, filtering, and linearization may be modified by reprogramming by the external programming unit. This processing circuitry may vary widely, so the following description of processing circuitry is merely exemplary.

A first amplifier 50 is used to amplify raw signal from the first rate-responsive sensor 22. The amplified signal from the first amplifier 50 is supplied to a first filter 52 used to minimize the effects of noise on the signal from the first rate-responsive sensor 22. The output of the first filter 52 is supplied to a first linearization circuitry 54, which serves to linearize the signal from the first rate-responsive sensor 22 if it varies in a nonlinear fashion. Such linearization circuitry is typically a nonlinear amplifier designed to correct the nonlinear response characterizing the sensor. The output of the first linearization circuitry 54 is a processed sensor 1 signal.

Similarly, a second amplifier 56 is used to amplify raw signal 2 from the second rate-responsive sensor 24. The amplified signal from the second amplifier 56 is supplied to a second filter 58 used to minimize the effects of noise on the signal from the second rate-responsive sensor 24. The output of the second filter 58 is supplied to a second linearization circuitry 60, which serves to linearize the signal from the second rate-responsive sensor 24 if it varies in a nonlinear fashion. The output of the second linearization circuitry 60 is a processed sensor 2 signal.

The outputs of the first linearization circuitry 54 and the second linearization circuitry 60 are supplied as inputs to processing and logic circuitry 61 used to analyze the processed sensor 1 signal and the processed sensor 2 signal. The output from the processing and logic circuitry 61 is supplied to a switch matrix 62, which uses the information supplied by the processing and logic circuitry 61 to select a particular set of numerical coefficients contained in a coefficient matrix 64.

In the example used herein to illustrate the present invention, there are three numerical coefficients which will be supplied from the coefficient matrix 64 to a computation logic circuit 66. The processed sensor 1 signal and the processed sensor 2 signal are also supplied to the computation logic circuit 66. The computation logic circuit 66 is used to calculate the selected rate based on a formula, which in the example herein is Rate $= X \cdot S_1 + Y \cdot S_2 + Z$, where X, Y, and Z are the three numerical coefficients, $S_1$ is the processed sensor 1 signal, $S_2$ is the processed sensor 2 signal, and Rate is the resulting pacemaker stimulating rate.

Thus, the processing and logic circuitry 61 and the switch matrix 62 are used to select a unique set of three numerical coefficients from the coefficient matrix 64. The first two numerical coefficients, X and Y, are weighting factors which will be multiplied by the processed sensor 1 signal and $S_2$ the processed sensor 2 signal, respectively. The third numerical coefficient, Z, is an offset factor. The third numerical coefficient may have a nonzero value, it may be zero, or, alternately, it may not be used at all; such a system would only have the first two numerical coefficients.

Thus, the output of the computation logic circuit 66 will be a calculated selected rate based both on the values of the processed sensor 1 signal and the processed sensor 2 signal, and on the analysis of these signals performed by the processing and logic circuitry 61. This will become more apparent below when an example of the processing and logic circuitry 61 is given in detail in conjunction with FIG. 3.

The selected rate is supplied as an input to a reaction and recovery time circuit 68. The reaction and recovery time circuit 68 serves both to limit the rate at which the pacing rate will be allowed to rise and the rate at which the pacing rate will be allowed to fall. Thus, the reaction and recovery time circuit 68 will mimic the natural operation of a healthy heart, which is limited in how fast it will change rate. The reaction and recovery time circuit 68 is thus used to rate_limit the selected rate output from the computation logic circuit 66. The output of the reaction and recovery time circuit 68 is the sensor-indicated rate signal.

An alternate approach to performing the reaction and recovery time functions would be to include these functions on the input side of the system rather than on the output side as shown herein. In a simpler system, the reaction and recovery time functions may be part of the initial signal processing, instead of being done after the rate matrix processing. In such a system, the slope of the input signals over time would be limited.

Figure 3:
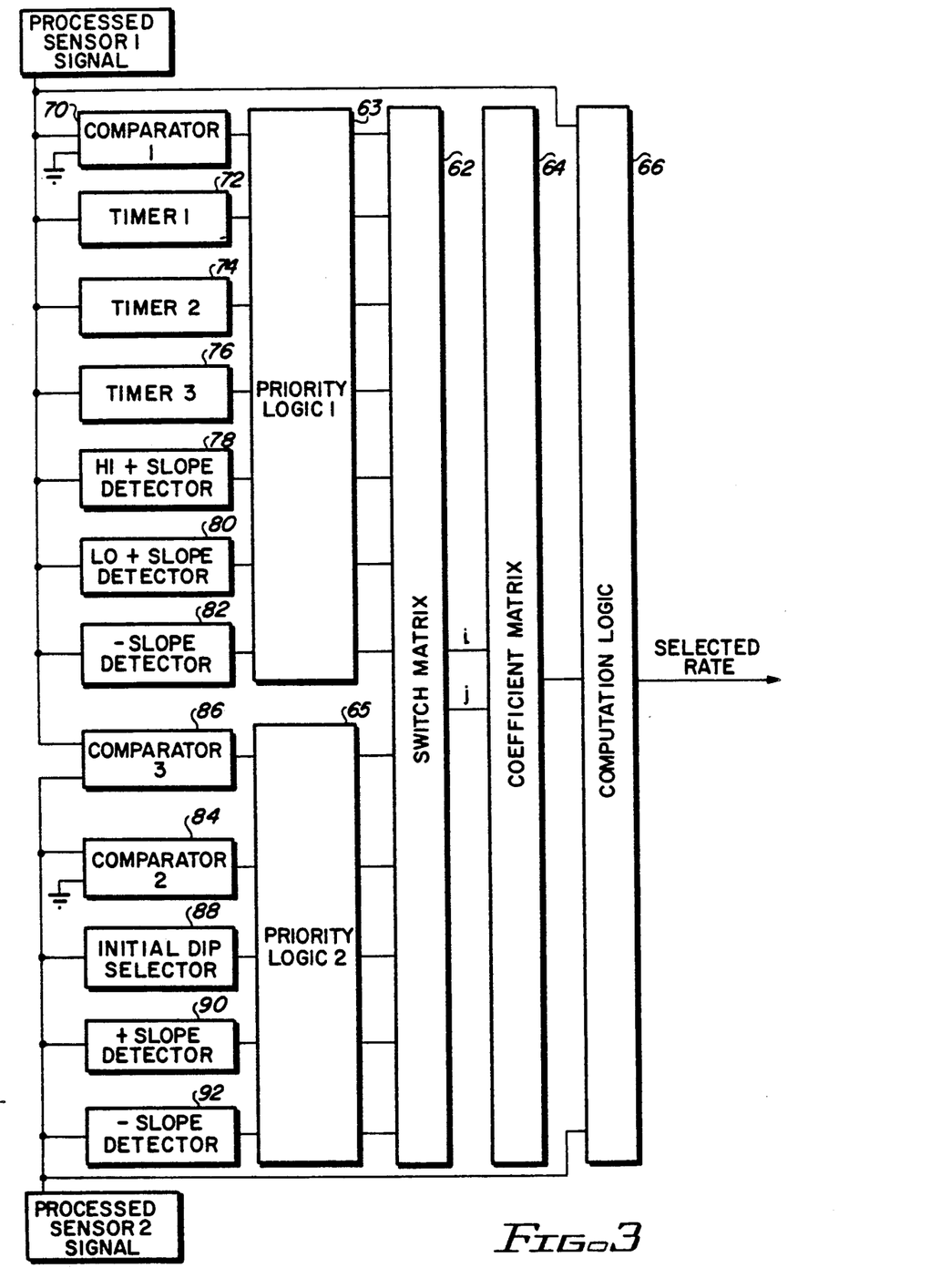
FIG. 3 is a functional block diagram of the preferred embodiment of the present invention illustrating an example of processing circuitry which may be used in the system of FIG. 2.

The criteria used to select which set of numerical coefficients is to be used may be various timing characteristics of the sensor response, or the satisfaction of various logic conditions. In the preferred embodiment a combination of these criteria is used. Referring to FIG. 3, an example of the processing and logic circuitry 61 is shown in which an activity sensor is utilized as the first rate-responsive sensor 22 (FIG. 1), and a temperature sensor is utilized as the second rate-responsive sensor 24 (FIG. 1). It will, of course, be realized by those skilled in the art that any combination of sensors could utilize the principles of operation of the present invention.

It is readily apparent from FIG. 3 that a number of processing circuits receive as inputs the processed sensor 1 signal and the processed sensor 2 signal. These processing circuits provide outputs which are supplied to either a first priority logic circuit 63 or a second priority logic circuit 65. The priority logic circuits 63 and 65 each provide an inputs on one of a plurality of lines to the switch matrix 62. These inputs enable the selection by the switch matrix 62 of a unique set of numerical coefficients. The output from the switch matrix 62 is a switch matrix row number i and a switch matrix column number j, which together identify a particular set of numerical coefficients contained in the coefficient matrix 64.

The function of the priority logic circuits 63 and 65 is to receive a number of inputs, more than one of which may be digital ones. The priority logic circuits 63 and 65 output signals on a plurality of lines, only one of which from each of the priority logic circuits 63 and 65 may be a digital one at any given time. Therefore, the priority logic circuits 63 and 65 each function to determine which one of a plurality of digital ones received as an input which should be provided as an output to the switch matrix 66.

Figure 4:
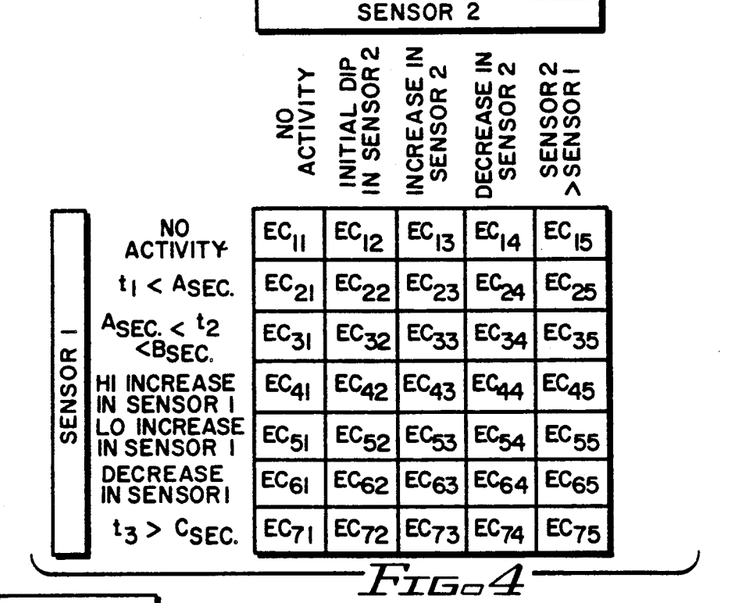
FIG. 4 is a 7 by 5 switch matrix illustrating the 35 different sets of equation coefficients which are selected according to the criteria implemented by the processing circuitry shown in FIG. 3.

The various processing circuitry supplying inputs to the switch matrix 62 may now be discussed. A first comparator 70 has as its input the processed sensor 1 signal, and is used to determine whether the processed sensor 1 signal indicated that no activity is being sensed. In FIG. 4 the other input is grounded, but it could be a small threshold signal as well. If no activity (or a level of activity below the threshold) is being sensed, then the first comparator 70 outputs a digital one signal to the first priority logic circuit 63.

A first timer 72 has as its input the processed sensor signal, and is used to determine whether activity has been sensed for less than A seconds. If activity has in fact been sensed for less than A seconds, then 72 outputs a digital one signal to the first priority logic circuit 63. A second timer 74 has as its input the processed sensor 1 signal, and is used to determine whether activity has been sensed for more than A seconds but less than B seconds, where B seconds is longer than A seconds. If activity has in fact been sensed for more than A seconds but less than B seconds, then the second timer 74 outputs a digital one signal to the first priority logic circuit 63.

A third timer 76 has as its input the processed sensor 1 signal, and is used to determine whether activity has been sensed for more than C seconds, where C seconds is a considerable length of time indicating prolonged exercise, or a false positive. If activity has in fact been sensed for more than C seconds, then the third timer 76 outputs a digital one signal to the first priority logic circuit 63.

A high positive slope detector 78 has as its input the processed sensor 1 signal, and is used to detect the existence of a high positive rate of change in the processed sensor signal. If this high positive rate of change in the processed sensor signal is detected by the high positive slope detector 78, and if activity has been sensed for more than B seconds but less than C seconds, then the high positive slope detector 78 outputs a digital one signal to the first priority logic circuit 63.

A low positive slope detector 80 has as its input the processed sensor 1 signal, and is used to detect the existence of a positive rate of change in the processed sensor 1 signal which is lower than that detected by the high positive slope detector 78. If this lower positive rate of change in the processed sensor 1 signal is detected by the low positive slope detector 80, and if activity has been sensed for more than B seconds but less than C seconds, then the low positive slope detector 80 outputs a digital one signal to the first priority logic circuit 63. The high positive slope detector 78 and the low positive slope detector 80 have mutually exclusive digital one outputs. A negative slope detector 82 has as its input the processed sensor 1 signal, and is used to detect the existence of a negative rate of change in the processed sensor 1 signal. If a negative rate of change in the processed sensor 1 signal is detected by the negative slope detector 82, and if activity has been sensed for more than B seconds but less than C seconds, then the negative slope detector 82 outputs a digital one signal to the first priority logic circuit 63.

The priority logic circuits 63 and 65 will determine the relative priority order of the input signals when several of the conditions have been met at the same time. They may also contain sequential circuitry which makes the priority order dependent on preceding inputs. The priority logic may be incorporated wholly or in part as part of the processing circuitry.

If there is a digital one signal from the first comparator 70, the first priority logic circuit 63 will pass this signal on to the switch matrix 66. If there is a digital one from the first timer 72, the first priority logic circuit 63 will pass this signal on to the switch matrix 66. If there is a digital one signal from the second timer 74, the first priority logic circuit 63 will pass this signal on to the switch matrix 66. If there is a digital one from the third timer 76, the first priority logic circuit 63 will pass this signal on to the switch matrix 66. Signals from the first comparator 70, the first timer 72, the second timer 74, and the third timer 76 are mutually exclusive.

If there is a digital one signal from the high positive slope detector 78, and there are no digital one signals from the first comparator 70, the first timer 72, the second timer 74, or the third timer 76 (indicating that activity has been sensed for more than B seconds but less than C seconds), the first priority logic circuit 63 will pass the signal from the high positive slope detector 78 on to the switch matrix 66.

If there is a digital one signal from the low positive slope detector 80, and there are no digital one signals from the first comparator 70, the first timer 72, the second timer 74, or the third timer 76 (indicating that activity has been sensed for more than B seconds but less than C seconds), the first priority logic circuit 63 will pass the signal from the low positive slope detector 80 on to the switch matrix 66.

If there is a digital one signal from the negative slope detector 82, and there are no digital one signals from the first comparator 70, the first timer 72, the second timer 74, or the third timer 76 (indicating that activity has been sensed for more than B seconds but less than C seconds), the first priority logic circuit 63 will pass the signal from the negative slope detector 82 on to the switch matrix 66. The comparator 70, the first timer 72, the second timer 74, the third timer 76, the high positive slope detector 78, the low positive slope detector 80, and 82 are all used to select the row of the switch matrix 62, as will become apparent below in the discussion in conjunction with FIG. 5. The remaining processing circuitry to be discussed is used to select the column of the switch matrix 62.

A second comparator 84 has as its input the processed sensor 2 signal, and is used to determine whether the processed sensor 2 signal indicated that no sensor 2 activity is being sensed. In FIG. 4 the other input is grounded, but it could be a small threshold signal as well. If no sensor 2 activity (or a level of activity below the threshold) is being sensed, then the second comparator 84 outputs a digital one signal to the second priority logic circuit 65.

A third comparator 86 has as inputs the processed sensor 1 signal and the processed sensor 2 signal. If the processed sensor 2 signal is greater than the processed sensor 1 signal, then the third comparator 86 outputs a digital one signal to the second priority logic circuit 65. (This of course would only happen when at least some activity was being sensed by sensor 2, indicating either a high body temperature in the absence of physical activity, or that the second sensor indicates a higher level of exercise than the first sensor. Thus, the second comparator 84 and the third comparator 86 have mutually exclusive digital one outputs.)

An initial dip detector 88 has as its input the processed sensor 2 signal, and is used to detect an initial dip in temperature characterized by a drop in the processed sensor 2 signal following a long period of inactivity of the processed sensor 2 signal. If this initial dip in the processed sensor 2 is detected by the initial dip detector 88, then the initial dip detector 88 outputs a digital one signal to the second priority logic circuit 65.

A positive slope detector 90 has as its input the processed sensor 2 signal, and is used to detect the existence of a positive rate of change in the processed sensor 2 signal. If a positive rate of change in the processed sensor 2 signal is detected by the positive slope detector 90, then the positive slope detector 90 outputs a digital one signal to the second priority logic circuit 65.

A negative slope detector 92 has as its input the processed sensor 2 signal, and is used to detect the existence of a negative rate of change in the processed sensor 2 signal. If a negative rate of change in the processed sensor 2 signal is detected by the negative slope detector 92, then the negative slope detector 92 outputs a digital one signal to the second priority logic circuit 65.

If there is a digital one signal from the second comparator 84, the second priority logic circuit 65 will pass this signal on to the switch matrix 66. If there is a digital one signal from the third comparator 86, the second priority logic circuit 65 will pass this signal on to the switch matrix 66. If there is a digital one signal from the initial dip detector 88, and if the output of the fourth comparator 86 is not a digital one signal, the second priority logic circuit 65 will pass the signal from the initial dip detector 88 on to the switch matrix 66.

If there is a digital one signal from the positive slope detector 90, and if the output of the fourth comparator 86 is not a digital one signal, the second priority logic circuit 65 will pass the signal from the positive slope detector 90 on to the switch matrix 66. If there is a digital one signal from the negative slope detector 92, and if the output of the fourth comparator 86 is not a digital one signal, and if the output of the initial dip detector 88 is not a digital one signal, the second priority logic circuit 65 will pass the signal from the positive slope detector 90 on to the switch matrix 66.

Referring now to FIG. 4 in addition to FIG. 3, the operation of the switch matrix 62 may be explained. The switch matrix shown in FIG. 4 is a 7 by 5 switch matrix used to select a specific set of numerical coefficients contained in the coefficient matrix 64. The selection of a cell in the rate matrix of FIG. 4 thus corresponds to the selection of a specific set of numerical coefficients intended to optimize the pacemaker rate for the specific conditions identified by the switch matrix.

The process used to select a specific cell in the switch matrix of FIG. 4 will now be explained. If the first comparator 70 outputs a signal which is provided by the first priority logic circuit 63 to the switch matrix 62, then the first row of the switch matrix of FIG. 4 will be chosen. If the first timer 72 outputs a signal which is provided by the first priority logic circuit 63 to the switch matrix 62, then the second row of the switch matrix of FIG. 4 will be chosen If the second timer 74 outputs a signal which is provided by the first priority logic circuit 63 to the switch matrix 62, then the third row of the switch matrix of FIG. 4 will be chosen.

If the high positive slope detector 78 outputs a signal which is provided by the first priority logic circuit 63 to the switch matrix 62, then the fourth row of the switch matrix of FIG. 4 will be chosen. If the low positive slope detector 80 outputs a signal which is provided by the first priority logic circuit 63 to the switch matrix 62, then the fifth row of the switch matrix of FIG. 4 will be chosen. If the negative slope detector 82 outputs a signal which is provided by the first priority logic circuit 63 to the switch matrix 62, then the sixth row of the switch matrix of FIG. 4 will be chosen. If the third timer 76 outputs a signal which is provided by the first priority logic circuit 63 to the switch matrix 62, then the seventh row of the switch matrix of FIG. 4 will be chosen.

If the second comparator 84 outputs a signal which is provided by the second priority logic circuit 65 to the switch matrix 62, then the first column of the switch matrix of FIG. 4 will be chosen. If the initial dip detector 88 outputs a signal which is provided by the second priority logic circuit 65 to the switch matrix 62, then the second column of the switch matrix of FIG. 4 will be chosen. If the positive slope detector 90 outputs a signal which is provided by the second priority logic circuit 65 to the switch matrix 62, then the third column of the switch matrix of FIG. 4 will be chosen.

If the negative slope detector 92 outputs a signal which is provided by the second priority logic circuit 65 to the switch matrix 62, then the fourth column of the switch matrix of FIG. 4 will be chosen. If the fourth comparator 86 outputs a signal which is provided by the second priority logic circuit 65 to the switch matrix 62, then the fifth column of the switch matrix of FIG. 4 will be chosen. This completes the selection of a cell, since both a row and a column will have been selected.

This description is made for explanatory purposes only. In a realistic system, the outputs from the individual sensor processing circuits defining certain conditions of each sensor signal would be interconnected to the switch matrix by a (programmable) logic circuit network which would establish the priority order of the detected conditions. For instance, following a time period with zero signal from the first sensor, the first timer 72 may be given priority over slope detectors 78, 80, and 82.

For example, if the second timer 74 outputs a signal through the first priority logic circuit 63 to the switch matrix 62 (indicating that activity has in fact been sensed for more than A seconds but less than B seconds), the third row in the switch matrix of FIG. 4 will be selected. If the third comparator 86 outputs a signal through the second priority logic circuit 65 to the switch matrix 62 (indicating that the processed sensor 2 signal is greater than the processed sensor signal), the fifth column in the switch matrix of FIG. 4 will be selected. Thus set of numerical coefficients $EC_{35}$ will have been selected.

The set of numerical coefficients $EC_{35}$, like all the other sets of numerical coefficients referenced in the switch matrix of FIG. 4, is contained in the coefficient matrix 64 of FIG. 3. Thus, the value of i supplied from the switch matrix 62 to the coefficient matrix 64 would be 3, and the value of j supplied from the switch matrix 62 to the coefficient matrix 64 would be 5.

The set of numerical coefficients selected are supplied from the coefficient matrix 64 to the computation logic circuit 66. It will be noted that the processed sensor 1 signal and the processed sensor 2 signal are also supplied to the computation logic circuit 66. Thus, following selection of the appropriate set of numerical coefficients X, Y, and Z, which are supplied to the computation logic circuit 66, the inputs of the processed sensor 1 signal and the processed sensor 2 signal will enable the computation logic circuit 66 to calculate the selected rate. That selected rate is then output from the computation logic circuit 66 to the memory containing rate matrices 68, which outputs the sensor-indicated rate signal.

It may thus be appreciated by those skilled in the art that the switch matrix 62 is used to analyze the particular circumstances indicated by the signals from the sensors. A set of numerical coefficients specifically designed for use under the particular circumstances is indicated, and that set of numerical coefficients from the coefficient matrix 64 as well as the processed signals from the sensors are supplied to the computation logic circuit 66, which calculates the selected rate. The selected rate is then used to control the pacing rate of the pacemaker 20.

In the example illustrated, the processed sensor 1 signal and the processed sensor 2 signal are both analog signals. This example is made in analog terms for clarity. In the preferred embodiment, the processed sensor 1 signal and the processed sensor 2 signal would be digital signals supplied to the processing and logic circuitry 61. In fact, the implementation of the control circuitry of the present invention could be either analog or digital circuitry, although digital circuitry is preferred.

The switch matrix 62 is a look-up memory device which accesses the coefficient matrix 64 (typically a RAM) to find the numerical coefficients. It will thus be appreciated by those skilled in the art that the system of the present invention has a unique set (or unique sets) of numerical coefficients for each unique output of the switch matrix 62. This represents a degree of versatility previously unknown in the art in utilizing inputs from two sensors, and is a tremendous improvement over the art.

The processed sensor 1 signal and the processed sensor 2 signal values will be sampled at regular intervals, followed by a look-up of the proper selected set of numerical coefficients in the rate matrix, and computation of the selected rate by the computation logic circuit 66. It is apparent that the overall transfer function implemented may be linear or nonlinear in any manner desired. If desired, a threshold value for one or both of the sensors may be built in, requiring the sensor signal to exceed a predetermined level before a rate change is implemented.

When using an activity sensor together with a slow metabolic sensor, it is easy to allow the activity sensor to have greater influence over the rate in the absence of sensed metabolic activity at the onset of exercise. Similarly, when metabolic activity is sensed, the metabolic sensor may be allowed to have greater influence over the rate than does the activity sensor. The versatility of this system thus retains the advantages of each sensor in a system which is truly better than the sum of its parts.

Similarly, the system may be used to combine signals from two sensors, one of which has a good specific response for low levels of exercise (low work levels) and the other of which has a good specific response for high levels of exercise (high work levels). The sensor which has a good response for low levels of exercise will be primarily in control during situations when the exercise level is low, and the sensor which has a good response for high levels of exercise will be primarily in control when the exercise level is high. Again, the advantages of each of the sensors are retained while the disadvantages are discarded by the system of the present invention.

It should be noted at this point that the utility of the present invention may be extended to systems using more than two sensors by using a switch matrix having more than two dimensions. Thus, for a system having three sensors, a three-dimensional switch matrix could be used. For each unique combination of processed sensor values, there will be a corresponding unique set of numerical coefficients.

In the preferred embodiment, the values of the various sets of numerical coefficients are programmable. An external programmer may be used to selectively program each of the sets of numerical coefficients stored in the rate matrix. The sets of numerical coefficients may thereby be tailored for different lifestyles, with factors such as age, activity level, and physical condition being used to select the values of the sets of numerical coefficients. The external programmer may embody an expert system in software to guide the physician to the proper matrix values for various different patient qualities.

In addition, the logic circuitry used to drive the switch matrix may also be programmable, at least to some extent. Time values may be programmable in the timers, for example. It may thus be appreciated that the system may be virtually fully programmable, if desired.

As an example of operation of the system, when a signal is first present from the activity sensor it may be allowed to drive the rate to a higher value in the absence of a change in the temperature signal. Thus, the numerical coefficient X, which is multiplied by the signal from the first (activity) sensor, would have a high value in this instance. (The numerical coefficient Y would be low in this instance.) For example, in the first 45 seconds of action in the activity signal, a high signal from the activity sensor with no activity indicated by a temperature sensor will be allowed to drive the rate of the pacemaker to a high rate.

Then, after such a time when one would anticipate a change in the temperature signal if body activity were in fact occurring, if there is no change in the temperature signal indicating activity, a different set of numerical coefficients having a lower value of X (and a higher value of Y) will be accessed, causing the selected rate to diminish. For example, in the interval between 45 and 90 seconds after the onset of the activity signal, a high signal from the activity sensor with no activity indicated by the temperature sensor would be allowed to drive the rate of the pacemaker to a moderate rate only.

Then, after a time interval when there would definitely be a change in the temperature signal if body activity were in fact occurring, if there is no change in the temperature signal indicating activity, still another set of numerical coefficients having a still lower value of X will be accessed, causing the selected rate to further diminish. For example, after 90 seconds from the onset of the activity signal, a high signal from the activity sensor with no activity indicated by the temperature sensor would be almost totally discarded, driving the pacemaker at or only slightly above the rest rate.

Figure 5:
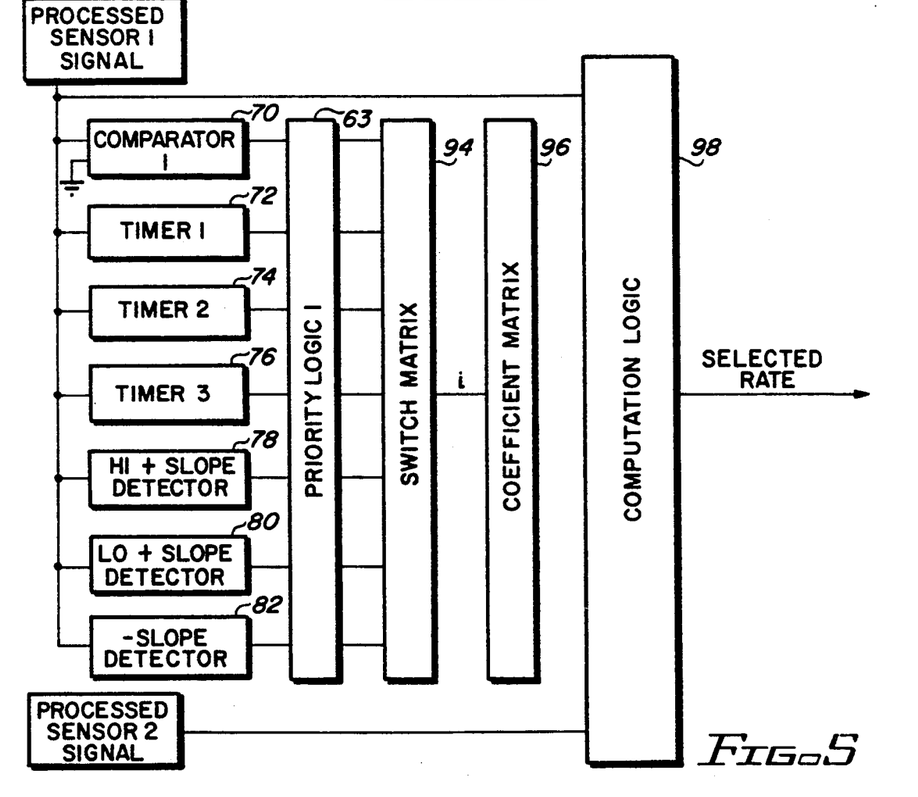
FIG. 5 is a functional block diagram of an alternate embodiment of the present invention having processing circuitry utilizing inputs from one of the sensors.

In an alternate embodiment differing from the embodiment in FIG. 3, a switch matrix may be used in conjunction with only one of the two sensor inputs to the system. Referring now to FIG. 5, the system of FIG. 3 is shown modified so that only the first sensor is used to operate the switch matrix. This configuration will work well when one sensor has a nearly ideal response with virtually no artifacts. One example of such a sensor is an oxygen saturation sensor. The example used in FIG. 5 again has an activity sensor utilized as the first rate-responsive sensor 22 (FIG. 1) and a temperature sensor utilized as the second rate-responsive sensor 24 (FIG. 1). It will, of course, be realized by those skilled in the art that any combination of sensors could utilize the principles of operation of the present invention.

It is readily apparent that a number of processing circuits receive as inputs the processed sensor 1 signal. These processing circuits provide outputs which are supplied through the first priority logic circuit 63 as inputs to a switch matrix 94. These inputs enable the selection by the switch matrix 94 of a unique set of numerical coefficients.

The various processing circuitry supplying inputs to the first priority logic circuit 63 are similar to those used in FIG. 3 for the first sensor input. The first comparator 70, the first timer 72, the second timer 74, the third timer 76, the high positive slope detector 78, the low positive slope detector 80, and the negative slope detector 82 are used to process the processed sensor 1 signal, and to supply inputs to the computation logic 98. The operation of these components is the same as explained above in conjunction with FIG. 3. The operation of the first priority logic circuit 63 is also the same as explained above in conjunction with FIG. 3.

Figure 6:
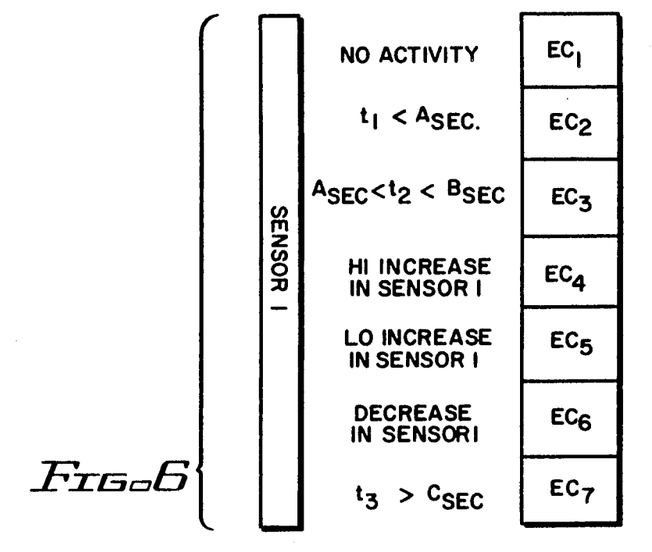
FIG. 6 is a 7 by 1 switch matrix illustrating the seven different sets of equation coefficients which are selected according to the criteria implemented by the processing circuitry shown in FIG. 5.

Referring now to FIG. 6 in addition to FIG. 5, the operation of the switch matrix 94 will be apparent. The switch matrix shown in FIG. 6 is a 7 by 1 switch matrix used to select a specific set of numerical coefficients contained in the memory 96. The output from the switch matrix 94 is a numerical coefficient set number i which identifies a particular set of numerical coefficients contained in the memory 96. The selected numerical coefficients are supplied to the computation logic 98 together with the processed signals from the sensors. The computation logic 98 calculates the value of the selected rate exactly as does the computation logic circuit 66 in FIG. 3.

The process used to select a specific cell in the switch matrix of FIG. 6 is analogous to the process used to select a specific row in the system of FIG. 3. If the first comparator 70 outputs a signal through the first priority logic circuit 63 to the switch matrix 94, then the first row of the switch matrix of FIG. 7 will be chosen. If the first timer 72 outputs a signal through the first priority logic circuit 63 to the switch matrix 94, then the second row of the switch matrix of FIG. 6 will be chosen. If the second timer 74 outputs a signal through the first priority logic circuit 63 to the switch matrix 94, then the third row of the switch matrix of FIG. 6 will be chosen.

If the high positive slope detector 78 outputs a signal through the first priority logic circuit 63 to the switch matrix 94, then the fourth row of the switch matrix of FIG. 6 will be chosen. If the low positive slope detector 80 outputs a signal through the first priority logic circuit 63 to the switch matrix 94, then the fifth row of the switch matrix of FIG. 6 will be chosen. If the negative slope detector 82 outputs a signal through the first priority logic circuit 63 to the switch matrix 94, then the sixth row of the switch matrix of FIG. 6 will be chosen. If the third timer 76 outputs a signal through the first priority logic circuit 63 to the switch matrix 94, then the seventh row of the switch matrix of FIG. 6 will be chosen. This completes the selection of a cell, since for the switch matrix of FIG. 6 only a row need be selected.

For example, if the second timer 74 outputs a signal through the first priority logic circuit 63 to the switch matrix 94 (indicating that activity has in fact been sensed for more than A seconds but less than B seconds), the third row in the switch matrix of FIG. 6 will be selected. Thus numerical coefficient set $EC_3$ will have been selected. The numerical coefficient set $EC_3$, like all the other sets of numerical coefficients referenced in the switch matrix of FIG. 5, is contained in the memory 96 of FIG. 5. Thus, the value of i supplied from the switch matrix 94 to the memory 96 would be 3. It will again be noted that the selected set of numerical coefficients, the processed sensor signal, and the processed sensor 2 signal are all supplied to the computation logic 98, which calculates the selected rate.

Thus, following selection of the appropriate set of numerical coefficients X, Y, and Z, the processed sensor 1 signal $S_1$ and the processed sensor 2 signal $S_2$ will be applied to the formula Rate $= X \cdot S_1 + Y \cdot S_2 + Z$. That formula will yield the selected rate, which is output from the computation logic 98. The balance of the operation is as explained with reference to FIGS. 1 and 2.

It may therefore be appreciated from the above detailed description of the preferred embodiment of the present invention that it teaches a system which will utilize inputs from two or more sensors to provide a sensor-indicated rate signal, which will control the pacing rate of the pacemaker. The system of the present invention utilizes the best properties of each of the sensors, while minimizing or eliminating their drawbacks. The control strategy is of a complexity sufficient to provide as an output a highly flexible sensor-indicated rate signal which will accurately follow a control strategy paralleling the physiological response of a healthy heart. In addition to being highly flexible, the control strategy of the preferred embodiment of the present invention is also fully programmable by using an external programmer.

The implementation of the present invention is relatively simple and easy to accomplish in a pacemaker, and will not increase the size of the pacemaker. The system of the present invention is useable with two sensors, and is capable of working with more than two sensors. The system is also economic of power, and does not require more power to operate than do other rate-response processors. Finally, all of the aforesaid advantages and objectives are achieved without incurring any substantial relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A rate-responsive pacemaker for stimulating the heart of a patient, said pacemaker comprising:
   pulse generating means for generating and delivering stimulation pulses to the patient's heart in response to a selected rate signal;
   a first sensor means for sensing a first physiological parameter of a patient and producing a first signal in response thereto;
   a second sensor means for sensing a second physiological parameter of a patient and producing a second signal in response thereto;
   first processing means for processing said first signal to provide a first switch matrix input signal indicative of one or more characteristics of said first signal;
   second processing means for processing said second signal to provide a second switch matrix input signal indicative of one or more characteristics of said second signal;
   an addressable switch matrix having as inputs said first and second switch matrix input signals and having as an output a unique set of numerical coefficients indicated by the values of said first and second switch matrix input signals; and
   means for computing a selected rate signal based on said first and second signals and said unique set of numerical coefficients, said selected rate signal being supplied to said pulse generating means.

2. A rate-responsive pacemaker as defined in claim 1, wherein said addressable switch matrix comprises:
   memory for storing a plurality of sets of numerical coefficients; and
   rate memory logic means for selecting the one of said plurality of sets of numerical coefficients stored in said memory which corresponds to the values of said first and second switch matrix input signals.

3. A rate-responsive pacemaker as defined in claim 2, wherein the values of said plurality of sets of numerical coefficients stored in said memory are programmable.

4. A rate-responsive pacemaker as defined in claim 2, wherein each of said plurality of sets of numerical coefficients comprises two numerical coefficients.

5. A rate-responsive pacemaker as defined in claim 4, wherein said numerical coefficients are weighting factors for said first and second signals.

6. A rate-responsive pacemaker as defined in claim 4, wherein said selected rate signal is calculated according to the formula $X \cdot S_1 + Y \cdot S_2$ where X and Y are the unique set of numerical coefficients, $S_1$ is the first signal, and $S_2$ is the second signal.

7. A rate-responsive pacemaker as defined in claim 2, wherein each of said plurality of sets of numerical coefficients comprises three numerical coefficients.

8. A rate-responsive pacemaker as defined in claim 7, wherein two of said numerical coefficients are weighting factors for said first and second signals, and the third of said numerical coefficients is an offset factor.

9. A rate-responsive pacemaker as defined in claim 8, wherein said selected rate signal is calculated according to the formula $X \cdot S_1 + Y \cdot S_2 + Z$ were X and Y are the two weighting factors in the unique set of numerical coefficients, $S_1$ is the first signal, $S_2$ is the second signal, and Z is the offset factor in the unique set of numerical efficients.

10. A rate-responsive pacemaker as defined in claim 1, wherein said first sensor means comprises:
    an activity sensor.

11. A rate-responsive pacemaker as defined in claim 10, wherein said second sensor means comprises:
    a temperature sensor.

12. A rate-responsive pacemaker as defined in claim 10, wherein said second sensor means comprises:
    a respiratory minute volume sensor.

13. A rate-responsive pacemaker as defined in claim 10, wherein said second sensor means comprises:
    a QT interval sensor.

14. A rate-responsive pacemaker as defined in claim 10, wherein said second sensor means comprises:
    a respiratory rate sensor.

15. A rate-responsive pacemaker as defined in claim 10 wherein said second sensor means comprises:
    a stroke volume sensor.

16. A rate-responsive pacemaker as defined in claim 10, wherein said second sensor means comprises:
    a blood pressure sensor.

17. A rate-responsive pacemaker as defined in claim 1, wherein one of said first and second sensor means comprises:
a blood oxygen saturation sensor.

18. A rate-responsive pacemaker as defined in claim 1, wherein one of said first and second sensor means comprises:
a blood oxygen partial pressure sensor.

19. A rate-responsive pacemaker as defined in claim 1 wherein said first sensor means has a relatively fast response and said second sensor means has a relatively slow response.

20. A rate-responsive pacemaker as defined in claim 19, wherein said first sensor means comprises one of the sensors from the group consisting of an activity sensor, a blood oxygen saturation sensor, a blood oxygen partial pressure sensor, and a p $CO_2$ sensor.

21. A rate-responsive pacemaker as defined in claim 19, wherein said second sensor means comprises one of the sensors from the group consisting of a respiratory minute volume sensor, a temperature sensor, a pH sensor, and a respiration rate sensor.

22. A rate-responsive pacemaker as defined in claim 1, wherein said first sensor means has a highly accurate response for low levels of exercise and said second sensor means has a highly accurate-response for high levels of exercise.

23. A rate-responsive pacemaker as defined in claim 22, wherein said first sensor means comprises one of the sensors from the group consisting of an activity sensor, a blood oxygen saturation sensor, a blood oxygen partial pressure sensor, and a $pCO_2$ sensor.

24. A rate-responsive pacemaker as defined in claim 22, wherein said second sensor means comprises one of the sensors from the group consisting of a respiratory minute volume sensor, a pH sensor, and a temperature sensor.

25. A rate-responsive pacemaker as defined in claim 1, wherein said first conversion means comprises:
a first amplifier for amplifying said first signal, said first amplifier having a first amplifier output;
a first filter for filtering said first amplifier output, said first filter having a first filter output; and
first linearizing means for linearizing said first filter output.

26. A rate-responsive pacemaker as defined in claim 1, wherein said second conversion means comprises:
a second amplifier for amplifying said second signal, said second amplifier having a second amplifier output;
a second filter for filtering said second amplifier output, said second filter having a second filter output; and
second linearizing means for linearizing said second filter output.

27. A rate-responsive pacemaker as defined in claim 1, additionally comprising: a reaction and recovery time circuit installed between said addressable rate matrix and said pulse generating means, said reaction and recovery time circuit for limiting the rate at which said selected rate signal supplied to said pulse generating means will be allowed to rise and fall.

28. A rate-responsive pacemaker for stimulating the heart of a patient, said pacemaker comprising:
pulse generating means for generating and delivering stimulation pulses to the patient's heart in response to a selected rate signal;
a first sensor means for sensing a first physiological parameter of a patient and producing a first signal in response thereto;
a second sensor means for sensing a second physiological parameter of a patient and producing a second signal in response thereto;
first processing means for processing said first signal to provide a first switch matrix input signal indicative of one or more characteristics of said first signal;
second processing means for processing said second signal to provide a second switch matrix input signal indicative of one or more characteristics of said second signal;
an addressable switch matrix having as inputs said first and second switch matrix input signals, said addressable switch matrix containing a plurality of sets of numerical coefficients therein, said addressable switch matrix having as an output a particular set of two numerical coefficients which is indicated in said addressable switch matrix by the values of said first and second switch matrix input signals; and
means for computing a selected rate signal by first computing the product of one of said two numerical coefficients and said first signal, secondly computing the product of the other of said two numerical coefficients and said second signal, and thirdly adding the products together, said selected rate signal being supplied to said pulse generating means.

29. A rate-responsive pacemaker for stimulating the heart of a patient, said pacemaker comprising:
pulse generating means for generating and delivering stimulation pulses to the patient's heart in response to a selected rate signal;
a first sensor means for sensing a first physiological parameter of a patient and producing a first signal in response thereto;
a second sensor means for sensing a second physiological parameter of a patient and producing a second signal in response thereto;
a third sensor means for sensing a third physiological parameter of a patient and producing a third signal in response thereto;
first processing means for processing said first signal to provide a first switch matrix input signal indicative of one or more characteristics of said first signal;
second processing means for processing said second signal to provide a second switch matrix input signal indicative of one or more characteristics of said second signal;
third processing means for processing said third signal to provide a third switch matrix input signal indicative of one or more characteristics of said third signal;
an addressable switch matrix having as inputs said first, second, and third switch matrix input signals and having as an output a unique set of numerical coefficients indicated by the values of said first, second, and third switch matrix input signals; and
means for computing a selected rate signal based on said first, second, and third signals and said numerical coefficients, said selected rate signal being supplied to said pulse generating means.

30. A rate-responsive pacemaker for stimulating the heart of a patient, said pacemaker comprising:

pulse generating means for generating and delivering stimulation pulses to the patient's heart in response to a selected rate signal;

a first sensor means for sensing a first physiological parameter of a patient and producing a first signal in response thereto;

a second sensor means for sensing a second physiological parameter of a patient and producing a second signal in response thereto;

first processing means for processing said first signal to provide a first switch matrix input signal indicative of one or more characteristics of said first signal;

an addressable switch matrix having as an input said first switch matrix input signal and having as an output a unique set of numerical coefficients indicated by the value of said first switch matrix input signal; and means for computing a selected rate signal based on said first and second signals and said numerical coefficients, said selected rate signal being supplied to said pulse generating means.

31. A method of selecting the stimulating rate of a rate-responsive pacemaker for stimulating the heart of a patient, comprising:

generating and delivering stimulation pulses to the patient's heart in response to a selected rate signal;

sensing a first physiological parameter of a patient and producing a first signal in response thereto;

sensing a second physiological parameter of a patient and producing a second signal in response thereto;

processing said first signal to provide a first switch matrix input signal indicative of one or more characteristics of said first signal;

processing said second signal to provide a second switch matrix input signal indicative of one or more characteristics of said second signal;

providing said first and second switch matrix input signals as inputs to an addressable switch matrix, said addressable switch matrix having as an output a unique set of numerical coefficients indicated by the values of said first and second switch matrix input signals; and computing a selected rate signal based on said first and second signals and said numerical coefficients, said selected rate signal being supplied to said pulse generating means.

* * * * *